(12) United States Patent
Kovesdi et al.

(10) Patent No.: US 6,514,943 B2
(45) Date of Patent: *Feb. 4, 2003

(54) METHOD AND COMPOSITION FOR PRESERVING VIRUSES

(75) Inventors: Imre Kovesdi, Rockville, MD (US); Stephen C. Ransom, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/870,920

(22) Filed: May 31, 2001

(65) Prior Publication Data

US 2002/0019041 A1 Feb. 14, 2002

Related U.S. Application Data

(63) Continuation of application No. PCT/US99/29271, filed on Dec. 10, 1999, which is a continuation-in-part of application No. 09/208,666, filed on Dec. 10, 1998, now Pat. No. 6,225,289.

(51) Int. Cl.[7] .................. A61K 31/70; A61K 47/00; A61K 48/00
(52) U.S. Cl. .................. 514/23; 514/777; 424/93.2
(58) Field of Search ............ 514/777, 23; 424/93.2

(56) References Cited

U.S. PATENT DOCUMENTS

| | | | |
|---|---|---|---|
| 3,674,864 A | 7/1972 | Angelucci | 424/90 |
| 3,915,794 A | 10/1975 | Zygraich et al. | 195/1.8 |
| 4,337,242 A | 6/1982 | Markus et al. | 424/89 |
| 4,338,335 A | 7/1982 | McAleer et al. | 424/361 |
| 4,678,812 A | 7/1987 | Bollin, Jr. et al. | 514/777 |
| 4,762,857 A | 8/1988 | Bollin, Jr. et al. | 514/777 |
| 4,891,319 A | 1/1990 | Roser | 435/188 |
| 5,149,653 A | 9/1992 | Roser | 435/260 |
| 5,364,756 A | 11/1994 | Livesey et al. | 435/2 |
| 5,792,643 A | 8/1998 | Herrmann et al. | 735/235.1 |
| 5,800,978 A | 9/1998 | Goodrich, Jr. et al. | 435/2 |
| 5,814,321 A | 9/1998 | Miyahara et al. | 424/278.1 |

FOREIGN PATENT DOCUMENTS

| | | |
|---|---|---|
| DE | 299 213 A | 4/1992 |
| EP | 415 567 A | 3/1991 |
| EP | 523 406 A | 1/1993 |
| EP | 872 249 A | 10/1998 |
| WO | WO 89/06542 A | 7/1989 |
| WO | WO 89/06976 A | 8/1989 |
| WO | WO 91/18091 A | 11/1991 |
| WO | WO 95/34671 A | 12/1995 |
| WO | WO 98/56414 A | 12/1998 |

OTHER PUBLICATIONS

Chu, *Chem. Abstr.*, 124CA:66573 (Nov. 16, 1995).
Croyle et al., *Pharmaceutical Development and Technology*, 3 (3), 373–383 (1998).
Curiel et al., *Hum. Gene Ther.*, 3, 147–154 (1992).
Davidson et al., *J. Virol.*, 61, 1226–1239 (1987).
Gupta et al., *Vaccine*, 14 (15), 1417–1420 (1996).
Liu et al., *Chem. Abstr.*, 126CA:308806 (Apr. 3, 1997).
Mansour et al., *Mol. Cell Biol.*, 6, 2684–2694 (1986).
Newman et al., *Biotechnology and Genetic Engineering Reviews*, 11, 263–294 (1993).
Paiva et al., *Biotechnology Annual Review*, 2, 293–314 (1996).
Sigma Chemical Catalog, Sigma Chemical company, St. Louis, MO, 1989, pp. 1679–80.*

* cited by examiner

*Primary Examiner*—Russell Travers
(74) *Attorney, Agent, or Firm*—Leydig, Voit & Mayer, Ltd.

(57) ABSTRACT

The present invention provides a method and a composition for preserving a virus. The virus is placed in a liquid carrier with a stabilizing agent selected from the group consisting of polysorbate 80, L-arginine, polyvinylpyrrolidone, trehalose, and combinations thereof. The liquid composition can be maintained at a temperature above 0° C. for a significant period of time while maintaining a satisfactory degree of viral activity.

64 Claims, No Drawings

METHOD AND COMPOSITION FOR PRESERVING VIRUSES

This application is a continuation of International Patent Application No. PCT/US99/29271, filed on Dec. 10, 1999, which is a continuation-in-part of U.S. patent application No. 09/208,666, filed Dec. 10, 1998, now U.S. Pat. No. 6,225,289.

TECHNICAL FIELD OF THE INVENTION

The present invention relates to methods and compositions useful in preserving viruses.

BACKGROUND OF THE INVENTION

Viruses (modified and unmodified) have several applications in modern biology wherein preservation (maintenance or storage) of the virus (for example in a virus stock or other composition comprising a virus) is desirable. Modified viruses (also referred to as viral vectors), for example, have proven convenient vector systems for investigative and therapeutic gene transfer applications. The use of viral vectors in investigative and therapeutic applications necessitates that the viral vectors be transported and stored for a period of time. During this period of storage, the viral vectors desirably are maintained without significant loss of infectivity, viability and/or the ability of the viral vector to produce a desired effect (e.g., stimulation of an immune response) or desired product, for example a viral polypeptide of interest. Unmodified viruses and other viral vectors are also useful in similar and other contexts, for example the production of an immune response to the virus, or to a component of the virus. In such contexts, preservation of the virus typically does not require retention of infectivity and/or viability of the virus, but rather the storage method can (and often seeks to) maintain (and even sometimes cause) the virus to be inactivated and/or attenuated, but stored in a manner wherein the desired property of the virus (e.g., immunogenecity of the virus or components thereof) is retained.

In the preservation of viable (active) viruses (e.g., viral vectors), it is known that viruses can be stored frozen at very low temperatures, e.g., −80° C., without significant loss of activity; however, the need for low temperature freezers, which are not widely available, limits the practicality of this approach. Lyophilization, or freeze-drying, is another known option for storage of viruses. This method has disadvantages as it is expensive, and, upon reconstitution, the virus composition is often left for extended periods of time at room temperature (i.e., 20–25° C.). In storage formulations presently known in the art, active viruses rapidly lose viability when stored at room temperature. Virus-containing compositions stored in containers in known formulations often lose viability within short periods of time. Similar problems arise when viral vectors are dried at room temperature or higher temperatures.

In view of the above, there exists a need for further methods of, and compositions useful in, the storage or preservation of viruses. In particular, there is a need for methods and compositions for storage of viruses in liquid compositions, rather than dried or frozen compositions, and in various containers. The present invention provides such methods and compositions. These and other advantages of the present invention, as well as additional inventive features, will be apparent from the description of the invention provided herein.

BRIEF SUMMARY OF THE INVENTION

The present invention provides a method and composition for preserving viruses, such as viral vectors. The present invention provides a method for preserving a virus comprising preparing a liquid composition comprising a virus, a liquid carrier, and a stabilizing agent selected from the group consisting of polysorbate 80, L-arginine, polyvinylpyrrolidone, trehalose, and combinations thereof, and subsequently maintaining the liquid composition at a temperature above 0° C. for at least 1 day. The present invention also provides a liquid composition comprising a virus, a liquid carrier, and a stabilizing agent selected from the group consisting of polysorbate 80, L-arginine, polyvinylpyrrolidone, trehalose, and combinations thereof, wherein the liquid composition can be maintained at a temperature above 0° C. for about 1 day without a decrease in viral activity greater than about 20%.

DETAILED DESCRIPTION OF THE INVENTION

The present invention provides a method for satisfactorily preserving (i.e., storing or maintaining) a virus in a liquid composition at a temperature above 0° C. for a period of time. The method comprises preparing a liquid composition comprising a virus, a liquid carrier, and a stabilizing agent, and subsequently maintaining the liquid composition at a temperature above 0° C. for at least 1 day. The present invention also provides a liquid composition comprising a virus, a liquid carrier, and a stabilizing agent, wherein the liquid composition can be maintained at a temperature above 0° C. for 1 day without a decrease in viral activity greater than about 20%.

The present invention can be practiced with any suitable virus, which includes both wild type viruses and modified viruses (i.e., viral vectors, such as viral gene transfer vectors). Examples of suitable viruses include, but are not limited to, Adenoviruses, Arboviruses, Astroviruses, Bacteriophages, Enteroviruses, Gastroenteritis Viruses, Hantavirus, Coxsackie viruses, Hepatitis A Viruses, Hepatitis B Viruses, Hepatitis C Viruses, Herpesviruses (for example, Epstein Barr Virus (EBV), Cytomegalovirus (CMV) and Herpes Simplex Virus (HSV)), Influenza Viruses, Norwalk Viruses, Polio Viruses, Rhabdoviruses, Reoviruses Rhinoviruses, Rotavirus, Retroviruses (e.g., A-type retroviruses such as HIV-1, HIV-2 and FeLV), and viruses of the genuses Baculoviridae, Caliciviridae, Caulimoviridae, Coronaviridae, Filoviridae, Flaviviridae, Hepadnaviridae, Nodaviridae, Orthomyxoviridae, Paramyxoviridae, Papovaviridae, Parvoviridae, Phycodnaviridae, Picomaviridae, and Togaviridae, and modified viruses (i.e., viral vectors such as adenoviral vectors) originating from, based upon, or substantially similar to any of the foregoing or other suitable virus. Other suitable viruses are known in the art and are well characterized. Examples of such other viruses can be found in, for example, Fields et al., *Virology* (3rd ed., Lippincott-Raven (1996)).

The present invention is particularly useful in maintaining a viral vector (as opposed to a wild type virus), e.g., a viral gene transfer vector for use in gene therapy. The viral vector can be any vector that, at least in some significant part, is (or is similar to) a wild type virus (e.g., a modified DNA vector of viral origin). Examples of suitable vectors include DNA viruses (e.g., adenoviral vectors) and RNA viral vectors (e.g., retroviral vectors). The virus preferably is an adenovirus and more preferably is an adenoviral vector. Most preferably, the virus is an adenoviral gene transfer vector (i.e., an adenovirus comprising at least one exogenous or modified gene).

The virus is maintained in a composition that is in liquid form. Preferably, the liquid composition is a pharmaceutical composition. The term "liquid" as used to describe the composition in the context of the present invention means consisting of, containing, covered with, or soaked with liquid that is not frozen solid. In other words, the composition is partially to completely liquid in nature, preferably completely liquid.

The liquid carrier can be any suitable liquid carrier, e.g., water. Preferably, the liquid carrier is a pharmaceutically acceptable liquid carrier, particularly when the liquid composition is a pharmaceutical composition. The pharmaceutically acceptable carrier can be a pharmaceutically acceptable liquid carrier that contains a buffer (e.g., a tris buffer) and a salt. Examples of suitable buffers and salts, as well as other types of pharmaceutically acceptable carriers, are well known in the art.

The stabilizing agent is selected from the group consisting of polysorbate 80, L-arginine, polyvinylpyrrolidone, $\alpha$-D-glucopyranosyl $\alpha$-D-glucopyranoside dihydrate (commonly known as trehalose), and combinations thereof. The stabilizing agent can be a single stabilizing agent or a combination of two or more stabilizing agents. Preferably, the stabilizing agent is trehalose alone, or a combination of trehalose with polysorbate 80. Of course, the liquid composition can comprise many other substances, for example other stabilizing agents, buffers, or carriers. In some embodiments of the present invention it is desirable that a saccharide other than trehalose is used in combination with trehalose (and/or other stabilizing agents).

The stabilizing agent can be present in the liquid composition in any suitable amount (e.g., concentration). When trehalose is used as the stabilizing agent, the trehalose desirably is present in the liquid composition in a concentration of about 2–10% (wt./vol.). More preferably, in such embodiments, the trehalose is present in a concentration of about 4–6% (wt./vol.). When trehalose and polysorbate 80 are both present in the liquid composition, the trehalose preferably is present in a concentration of 4–6% (wt./vol.), more preferably about 5% (wt./vol.), while the polysorbate 80 desirably is present in a concentration of about 0.001–0.01% (wt./vol.), more preferably about 0.0025% (wt./vol.).

The term "activity" is used herein with reference to viability (e.g., actual and/or potential viability) of the virus. The present invention can be utilized to preserve (e.g., store) either "active" and/or "inactive" viruses. The term "activity," as used in describing embodiments of the present invention in which the virus is retained in (or at least can be reconstituted to) an active state, refers to any suitable measure of the viability of a composition of a virus. Numerous measurements of virus activity are known in the art and can be used within the context of the present invention. At any particular time of testing, some time can be required to test the virus's activity (e.g., sufficient time for the viral vector to exhibit the characteristic to be measured). For example, if the test time is day zero (for example, a cell is infected with a virus and subsequently stored in the liquid composition on the same day), some time may be required on that day in order to observe the measured trait.

An example of a suitable measure of virus activity (and thus the activity of the liquid composition) is the infectivity of the virus. Infectivity can be determined by any number of suitable assays known in the art. Infectivity can involve determining the number of infected cells of a cell population contacted with a certain concentration of virus at a particular time. Infectivity also can be determined by a standard plaque assay at different times using similar amounts of the virus (or composition comprising the virus) and similar cell media. The plaque assay is a classical virological technique, originally developed for bacteriophages by Felix d'Herelle in 1917 and subsequently altered by Dulbecco and Vogt for mammalian viruses, and still widely used for determination of viral titers by observing the infectivity of the virus (or vectors) in a given composition (or stock).

It is often desirable to use techniques different from or building upon the cell count or standard plaque assay, such as modified plaque assays, or combining the assay with the use of a computer program to facilitate determination of activity. Other suitable, and often preferred, assays for determining activity include performing immunological assays of the production of antiviral antibodies by a cell (e.g., by using an ELISA or Western Blot assay) and measuring the production of cytokines (e.g., interferons) generated in response to the introduction of the virus into a given host. When infectivity of the virus is used as an assessment of activity, a suitable amount of time needs to be allowed for viral infection of a population of cells to occur prior to the determination of infectivity.

Alternatively, viral activity can be determined by examining the ability of the virus to produce products within a host cell, e.g., a specific viral protein, polypeptide, glycoprotein, or RNA. When the virus is a viral gene transfer vector, activity desirably is a measure of the amount of gene product produced by cells (e.g., 293 cells or preferably A549 cells) infected by a sample comprising the viral gene transfer vector. The measurement of such a virus protein or other product (as with other measurements of activity) can be carried out by any suitable technique. For example, the micrograms of product produced per microliter of liquid composition can be determined under similar conditions at different test times.

The precise measurement technique for viral activity will depend, to some extent, upon the particular liquid composition, especially the particular virus preserved therein, e.g., the nature of the viral gene transfer vector and product(s) produced thereby. One of ordinary skill in the art can readily determine and utilize appropriate viral activity measurement techniques. Indeed, techniques to perform the above-discussed assays are widely known in the art. Such techniques are discussed further, for example, in Fields et al., *Virology* (3rd ed., Lippincott-Raven (1996)), and Sambrook et al., *Molecular Cloning: A Laboratory Manual*, Cold Spring Harbor Laboratory Press, NY (1989).

The temperature at which the liquid composition is maintained can be any suitable temperature to maintain the virus in its desired state over the time period of storage. Typically, the liquid composition is maintained at a temperature above 0° C., (e.g., at a temperature of 2° C., 4° C., 10° C., 20° C., 28° C., or 37° C., or higher than any of the foregoing), preferably at 2° C. or higher (e.g., 2–10° C.), and more preferably at 4° C. or higher (e.g., 4–10° C.). The liquid composition also can be maintained at a temperature of 10° C. or higher (e.g., 10–20° C.), 20° C. or higher (e.g., 20–25° C.), or even 30° C. or higher (e.g., 30–40° C.), such as may be encountered under non-environmentally controlled ambient conditions (which can result in the virus composition being exposed to a variety of non-freezing temperatures of, for example, 4–37° C.).

The virus can be maintained in the liquid composition for various periods of time. The liquid composition desirably is maintained at any of the aforementioned temperatures for at least 1 day (e.g., 7 days (1 week) or more). Typically, the time period will be longer, such as at least 3, 4, 5, or 6 weeks, or even longer, such as at least 10, 20, 30, 40, or 50 weeks.

The present invention allows for the preservation of viral activity during storage of a virus at any of the aforementioned temperatures and for any of the aforementioned time periods. When the retention of viral activity is desired (e.g., when the virus is a viral gene transfer vector), the present invention desirably allows for no significant or substantial (if any) decrease in viral activity at any of the aforementioned storage temperatures and for any of the aforementioned time periods, although some loss of viral activity is acceptable, especially with relatively higher storage temperatures and/or relatively longer storage times. More particularly, the present inventive method and composition desirably preserve a virus at any of the aforementioned temperatures and for any of the aforementioned time periods without a decrease in viral activity of greater than about 50%, preferably without a decrease in viral activity of greater than about 40%, and more preferably without a decrease in viral activity of greater than about 30%. In some embodiments, especially at relatively lower temperatures and/or for relatively shorter periods of time, the present inventive method and composition desirably preserve a virus at any of the aforementioned temperatures and for any of the aforementioned time periods without a decrease in viral activity of greater than about 20%, preferably without a decrease in viral activity of greater than about 10%, and more preferably without a decrease in viral activity of greater than about 5%.

In some instances, the retention of viral activity is not necessary or not desirable (for example, when the virus is used to induce an immune response). Thus, the liquid composition can be maintained at a temperature and for a period of time such that the inactivation or attenuation of the virus occurs and/or is suitably maintained, but wherein the virus is still suitable for its intended end-use after the storage time period (e.g., a desired immune response is still effectuated by the virus after the storage time period).

The liquid composition can possess any suitable pH. A suitable pH in the context of the present invention is any pH where the virus is maintained in the liquid composition in a state capable of being later used for its intended purpose (e.g., gene expression to produce a protein or stimulation of an immune response). The pH of the liquid composition desirably is about 6–9, e.g., about 6–8.5, although the liquid composition can have a lower or higher pH, particularly with the use of buffers. The liquid composition preferably has a pH of about 7–8.5, more preferably about 7.5–8, and most preferably about 7.8. The liquid composition with a pH somewhat above 7 (e.g., about 7.6 or about 7.8) but below about 8.5 is particularly preferred when the liquid composition is stored in a tris buffer at higher temperatures inasmuch as decreases in pH in tris buffers are commonly associated with elevated temperatures (e.g., about 28° C. or 37° C.). Moreover, in pharmaceutical compositions it is also desirable to maintain pH at or above 7 to avoid negative physical side effects known to be associated with compositions of lower pH introduced into mammalian hosts, particularly humans.

If the preservation of viral activity is not necessary and/or not desirable (such as for the storage of inactivated or attenuated virus), the pH of the liquid composition desirably may be above or below the range desirable for retention of virus activity (e.g., below about pH 6 or above about pH 8.5), as long as the pH remains in a suitable range for the storage of the virus for its intended use (e.g., causing an immune response). For example, if the virus is an inactivated or attenuated virus for use in stimulating an immune response, the liquid composition can be maintained at a pH (and/or a temperature) such that the attenuated or inactivated virus is maintained in its attenuated or inactivated state.

The liquid composition can be placed (e.g., maintained or stored) in any suitable container. Typically, the container will comprise, consist essentially of, or consist of glass or plastic. The plastic can be composed of, for example, any suitable polymer, particularly a polyolefin, such as polypropylene or polyethylene, especially polypropylene. The container can be silanized or have a coating thereon.

EXAMPLES

The present invention is further described in the following examples. The examples serve only to illustrate the invention and are not intended to limit the scope of the invention in any way.

Example 1

This example compares the effect of various saccharides on the preservation of a viral vector composition.

A series of liquid compositions was prepared. Each composition contained an adenoviral vector, water, 10 mM Tris (pH 7.8 at room temperature (i.e., 20–25° C.)), 75 mM NaCl, and 2% (wt./vol.), 3% (wt./vol.), 5% (wt./vol.), or 10% (wt./vol.) of one of the following saccharides: sorbital, trehalose, sucrose, mannitol, or dextrose. The adenoviral vector was E1 and E3 deficient with a reporter gene, secretory alkaline phosphatase (SEAP), under control of the cytomegalovirus (CMV) promoter, inserted in the E1 region. Each composition was stored at 37° C. for 7 days, and then the activity of the composition was determined. Activity was determined by measuring the amount of SEAP produced upon infection of A549 cells with a sample of the adenoviral vector composition. The percent decrease in activity for each composition is set forth in Table 1.

TABLE 1

| Saccharide | Percent Decrease in Activity of Adenoviral Vectors Stored at 37° C. for 7 Days | | | |
|---|---|---|---|---|
| | 2% wt./vol. | 3% wt./vol. | 5% wt./vol. | 10% wt./vol. |
| Sorbital | 100 | 100 | 99 | 99 |
| Trehalose | 57 | 42 | 28 | 25 |
| Sucrose | 100 | 100 | 100 | 99 |
| Mannitol | 100 | 100 | 100 | 99 |
| Dextrose | 100 | 100 | 100 | 100 |

As is apparent from the experimental results set forth in Table 1, trehalose was the most effective stabilizing agent for the adenoviral vector stored for seven days at 37° C. The other saccharides—sorbital, sucrose, mannitol and dextrose—exhibited little or no stabilizing effect on the adenoviral vectors. These results demonstrate that trehalose stabilizes viral vector compositions sufficiently such that the viral vectors can be stored for 7 days at non-environmentally controlled ambient conditions, e.g., at temperatures of up to 37° C. Similar experiments have been performed with the vascular endothelial growth factor (VEGF) gene inserted in the E1 region of the adenoviral vector in place of the SEAP gene and similar results as those described herein were also observed. Moreover, these results demonstrate that trehalose is superior to other saccharides (sorbital, mannitol and dextrose) and disaccharides (sucrose) in preserving the activity of virus-containing compositions.

Example 2

This example illustrates the ability of trehalose to stabilize a virus-containing composition.

Liquid compositions were prepared in accordance with Example 1, except that only trehalose was used as the stabilizing agent at a concentration of 5% (wt./vol.). The compositions were stored at various temperatures—4° C., 25° C., or 37° C.—for various periods of time—1 day, 1 week, 3 weeks, 6 weeks, 11 weeks, 19 weeks, 21 weeks, 31 weeks, 41 weeks, and 52 weeks—in a liquid state. The activity of each composition was determined in the same manner as set forth in Example 1 after the indicated storage period, and the percent decrease in activity for each composition is set forth in Table 2.

TABLE 2

| | Percent Decrease in Activity of Adenoviral Vectors Stored with 5% (wt./vol.) Trehalose | | |
|---|---|---|---|
| Time | 4° C. | 25° C. | 37° C. |
| 1 day | 2 | 7 | 0 |
| 1 week | 2 | 23 | 66 |
| 3 weeks | 2 | 28 | 90 |
| 6 weeks | 0 | 53 | 100 |
| 11 weeks | 10 | 79 | 100 |
| 19 weeks | 15 | 94 | 100 |
| 21 weeks | 15 | 97 | 100 |
| 31 weeks | 15 | 100 | 100 |
| 41 weeks | 16 | 100 | 100 |
| 52 weeks | 18 | 100 | 100 |

As is apparent from the experimental results set forth in Table 2, 5% (wt./vol.) trehalose was most effective in stabilizing the adenoviral vector under 4° C. storage conditions. The activity of the adenoviral vector composition after 11 weeks had decreased only about 10%, and at 52 weeks had decreased only about 18%. At room temperature (i.e., 20–25° C.), the activity of the adenoviral vector composition had decreased about 25% after 1 week, about 79% after 11 weeks, and about 100% by 31 weeks. For the adenoviral vector compositions stored at 37° C., the activity decreased about 70% after 1 week and about 100% after 6 weeks. These results demonstrate that 5% (wt./vol.) trehalose stabilizes an active virus at a range of temperatures and for extended periods of time.

Example 3

This example illustrates the ability of trehalose and polysorbate 80 to act as a stabilizing agent for active viruses.

Liquid compositions were prepared in accordance with Example 1, except that 5% (wt./vol.) trehalose and 0.0025% (wt./vol.) polysorbate 80 were used as the stabilizing agent. The compositions were stored and evaluated in the same manner as set forth in Example 2. The activity of each composition was determined in the same manner set forth in Example 1 after the indicated storage period, and the percent decrease in activity for each composition is set forth in Table 3.

TABLE 3

| | Percent Decrease in Activity of Adenoviral Vectors Stored with Trehalose and Polysorbate 80 | | |
|---|---|---|---|
| Time | 4° C. | 25° C. | 37° C. |
| 1 day | 0 | 5 | 14 |
| 1 week | 0 | 6 | 41 |
| 3 weeks | 5 | 25 | 84 |
| 6 weeks | 0 | 44 | 100 |
| 11 weeks | 5 | 77 | 100 |
| 19 weeks | 6 | 92 | 100 |
| 21 weeks | 8 | 96 | 100 |
| 31 weeks | 6 | 100 | 100 |
| 41 weeks | 6 | 100 | 100 |
| 52 weeks | 7 | 100 | 100 |

As is apparent from the experimental results set forth in Table 3, trehalose and polysorbate 80 were most effective in stabilizing the adenoviral vector under 4° C. storage conditions. After 1 week, the activity of the adenoviral vector composition had not significantly diminished; after 11 weeks, the activity had only decreased about 5%, and even after 52 weeks the activity of the adenoviral vector composition had only decreased about 7%. At room temperature (i.e., 20–25° C.), the activity of the adenoviral vector composition had decreased about 50% after 6 weeks, and about 80% after 11 weeks. For the adenoviral vector compositions stored at 37° C., the activity decreased about 40% after 1 week, and about 85% after 3 weeks. These results demonstrate that trehalose and polysorbate 80 are effective at stabilizing an active virus (e.g., a viral vector) at a range of temperatures for extended periods of time.

Example 4

This example further illustrates the ability of various excipients to stabilize viral vector compositions.

Three liquid compositions were prepared in a manner similar to that set out in Example 1. Each composition contained an adenoviral vector, water, 10 mM Tris (pH 7.8 at room temperature (i.e., 20–25° C.)), 75 mM NaCl, 3% (wt./vol.) sucrose, and either 0.0025% (wt./vol.) polysorbate 80, 20 mM L-arginine, or 0.1% (wt./vol.) polyvinylpyrrolidone. Each composition was stored at 37° C. for 4 days, and then the activity of the composition was determined in the same manner as set forth in Example 1. The percent decrease in activity for each composition is set forth in Table 4.

TABLE 4

| Stabilizer | Percent Decrease in Activity of Adenoviral Vectors Stored at 37° C. for 4 Days |
|---|---|
| Polysorbate 80 | 31 |
| L-arginine | 42 |
| Polyvinylpyrrolidone | 53 |

As is apparent from the experimental results set forth in Table 4, polysorbate 80 had a stabilizing effect on the activity of adenoviral vectors (about 30% activity decrease), while L-arginine and polyvinylpyrrolidone exhibited somewhat less of a stabilizing effect on the adenoviral vector at 37° C. (about 40% and 50% activity decreases, respectively). These results demonstrate that polysorbate 80, L-arginine, and polyvinylpyrrolidone can be useful, alone or preferably in combination with other stabilizing agents, in preserving active viruses, e.g., viral vectors.

Example 5

This example demonstrates the superior ability of trehalose alone and in conjunction with polysorbate 80 to stabilize viral vectors in glass and plastic containers.

Liquid compositions were prepared in a manner similar to that set out in Example 1. Each composition contained an adenoviral vector, water, 10 mM Tris (pH 7.8 at room temperature (i.e., 20–25° C.)), 75 mM NaCl, and either 3% sucrose, 5% trehalose, or a combination of 5% trehalose and 25 ppm polysorbate 80. A composition also was prepared with the adenoviral vector, water, 10 mM Tris (pH 7.8 at room temperature (i.e., 20–25° C.)), 150 mM NaCl, 10 mM $MgCl_2$, and 3% sucrose. Samples of each composition were placed into plastic (polypropylene) containers, and relatively equivalent samples of each composition were placed into glass containers. The samples of the compositions were then stored at either 4° C. or 25° C., and the activities of the compositions were determined at various points of time, i.e., initially (0 weeks), at 3 weeks, at 6 weeks, and at 11 weeks, as well as at 1 day and at 1 week for those compositions in the plastic containers. The activities of the compositions were determined in the same manner set forth in Example 1. The percent decrease in activity for each composition is set forth in Tables 5a and 5b.

trehalose and polysorbate 80 provided as good, if not better, retention of the activity of the adenoviral vector composition in a glass container (about 0–10% activity decrease at 4° C. and 25° C. after 3 weeks). Trehalose alone and in combination with polysorbate 80 was particularly effective at retaining adenoviral vector composition activity at lower temperatures in glass containers (about 10–20% activity decrease at 4° C. after 11 weeks). In contrast, sucrose did not ensure good retention of the activity of the adenoviral vector composition in a glass container (about 50–85% activity decrease at 4° C. and 25° C. after only 3 weeks and about 80–95% activity decrease at 4° C. after 11 weeks).

The results set forth in Table 5b show that trehalose alone or with polysorbate 80 as the stabilizing agent also had a similar superior stabilizing effect on the activity of adenoviral vectors stored in plastic containers (about 0–30% activity decrease at 4° C. and 25° C. after 3 weeks). The adenoviral vector compositions maintained with sucrose as the stabilizing agent in plastic containers lost all viral activity under the same conditions.

These results further demonstrate that the difference in the ability of trehalose alone and with polysorbate 80 to preserve the adenoviral vector in plastic containers, compared to the other compositions tested, was significantly greater than the differences observed in glass containers. For TABLE 5a Percent Decrease in Activity of Adenoviral Vectors Stored in Glass Containers in Various Compositions Over Time

|  | Trehalose & Polysorbate 80 at 4° C. | Trehalose & Polysorbate 80 at 25° C. | Trehalose at 4° C. | Trehalose at 25° C. | Sucrose at 4° C. | Sucrose at 25° C. | Sucrose & $MgCl_2$ at 4° C. | Sucrose & $MgCl_2$ at 25° C. |
|---|---|---|---|---|---|---|---|---|
| 0 Weeks | 0 | 0 | 0 | 0 | 0 | 0 | 0 | 0 |
| 3 Weeks | 0 | 9 | 11 | 25 | 51 | 70 | 53 | 84 |
| 6 Weeks | 0 | 45 | 6 | 44 | 48 | 75 | 73 | 95 |
| 11 Weeks | 16 | 71 | 10 | 74 | 81 | 99 | 94 | 100 |

TABLE 5b

Percent Decrease in Activity of Adenoviral Vectors Stored in Plastic Containers in Various Compositions Over Time

|  | Trehalose & Polysorbate 80 at 4° C. | Trehalose & Polysorbate 80 at 25° C. | Trehalose at 4° C. | Trehalose at 25° C. | Sucrose at 4° C. | Sucrose at 25° C. | Sucrose & $MgCl_2$ at 4° C. | Sucrose & $MgCl_2$ at 25° C. |
|---|---|---|---|---|---|---|---|---|
| 0 Weeks | 0 | 0 | 0 | 0 | 0 | 0 | 0 | 0 |
| 1 Day | 0 | 6 | 3 | 8 | 74 | 81 | 79 | 95 |
| 1 Week | 1 | 8 | 3 | 24 | 100 | 100 | 99 | 100 |
| 3 Weeks | 7 | 27 | 2 | 29 | 100 | 100 | 100 | 100 |
| 6 Weeks | 0 | 46 | 0 | 54 | 100 | 100 | 100 | 100 |
| 11 Weeks | 7 | 77 | 9 | 79 | 100 | 100 | 100 | 100 |

As is apparent from the experimental results set forth in Table 5a, trehalose alone had a significant stabilizing effect on the activity of adenoviral vectors stored in glass containers (about 10–25% activity decrease at 4° C. and 25° C. after 3 weeks). The results further indicate that the combination of example, the sucrose-containing compositions had about 100% reduction in viral activity at 4° C. after only 3 weeks in the plastic container compared to about 50% reduction in viral activity under the same conditions in the glass container, whereas the trehalose-containing compositions performed similarly in both the plastic and glass containers with only about 0–10% viral activity decrease at 4° C. after 3 weeks.

These results demonstrate that trehalose can be useful, alone or preferably in combination with polysorbate 80, in preserving viral vector compositions in both plastic and glass containers. Moreover, these results demonstrate that the present invention provides significantly better retention of viral vector composition activity in both plastic and glass containers than other compositions.

All of the references cited herein, comprising patents, patent applications, and publications, are hereby incorporated in their entireties by reference. The use of the terms "a," "an," "the," and similar referents (e.g., "an adenoviral vector" or "a liquid composition") in the context of describing the present invention (especially in the context of the following claims) are intended to cover both the singular and the plural, unless otherwise indicated herein or clearly contradicted by context.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention comprises all modifications encompassed within the spirit and scope of the invention as defined by the following claims.

What is claimed is:

1. A method of preserving an adenovirus, the method comprising:
    (a) preparing a liquid composition comprising
        (i) an adenovirus,
        (ii) a liquid carrier, and
        (iii) a stabilizing agent selected from the group consisting of polysorbate 80, L-arginine, polyvinylpyrrolidone, trehalose, and combinations thereof, and
    (b) maintaining the liquid composition at a temperature above 0° C. for at least 1 day.

2. The method of claim 1, wherein the liquid composition comprises trehalose.

3. The method of claim 2, wherein the trehalose is present in the liquid composition in a concentration of about 2–10% (wt./vol.).

4. The method of claim 2, wherein the liquid composition further comprises polysorbate 80.

5. The method of claim 2, wherein the liquid composition further comprises a saccharide other than trehalose.

6. The method of claim 4, wherein the liquid composition further comprises a saccharide other than trehalose.

7. The method of claim 1, wherein the liquid composition is maintained at a temperature above 0° C. for at least 7 days without a decrease in viral activity of greater than about 20%.

8. The method of claim 1, wherein the liquid composition is maintained at a temperature of about 28° C. or higher for at least 7 days without a decrease in viral activity of greater than about 50%.

9. The method of claim 1, wherein the liquid composition is maintained at a temperature above 0° C. for at least 10 weeks without a decrease in viral activity of greater than about 50%.

10. The method of claim 1, wherein the liquid composition is a pharmaceutical composition, the liquid carrier is a pharmaceutically acceptable liquid carrier, and the adenovirus is an adenoviral gene transfer vector.

11. The method of claim 1, wherein the liquid composition is maintained in a plastic container.

12. A liquid composition comprising:
    (i) an adenovirus,
    (ii) a liquid carrier, and
    (iii) a stabilizing agent selected from the group consisting of polysorbate 80, L-arginine, polyvinylpyrrolidone, trehalose, or a combination thereof, wherein the liquid composition can be maintained at a temperature above 0° C. for 1 day without a decrease in viral activity of greater than about 20%.

13. The liquid composition of claim 12, wherein the liquid composition comprises trehalose.

14. The liquid composition of claim 13, wherein the trehalose is present in the liquid composition in a concentration of about 2–10% (wt./vol).

15. The liquid composition of claim 13, wherein the liquid composition further comprises polysorbate 80.

16. The liquid composition of claim 13, wherein the liquid composition further comprises a saccharide other than trehalose.

17. The liquid composition of claim 15, wherein the liquid composition further comprises a saccharide other than trehalose.

18. The liquid composition of claim 12, wherein the liquid composition can be maintained at a temperature above 0° C. for at least 7 days without a decrease in viral activity of greater than about 20%.

19. The liquid composition of claim 12, wherein the liquid composition can be maintained at a temperature of about 28° C. or higher for at least 7 days without a decrease in viral activity of greater than about 50%.

20. The liquid composition of claim 12, wherein the liquid composition can be maintained at a temperature above 0° C. for at least 10 weeks without a decrease in viral activity of greater than about 50%.

21. The liquid composition of claim 18, wherein the liquid composition has been maintained at a temperature above 0° C. for at least 7 days without a decrease in viral activity of greater than about 20%.

22. The liquid composition of claim 19, wherein the liquid composition has been maintained at a temperature of about 28° C. or higher for at least 7 days without a decrease in viral activity of greater than about 50%.

23. The liquid composition of claim 20, wherein the liquid composition has been maintained at a temperature above 0° C. for at least 10 weeks without a decrease in viral activity of greater than about 50%.

24. The liquid composition of claim 12, wherein the liquid composition is a pharmaceutical composition, the liquid carrier is a pharmaceutically acceptable liquid carrier, and the adenovirus is an adenoviral gene transfer vector.

25. The liquid composition of claim 12, wherein the liquid composition is maintained in a glass container.

26. The liquid composition of claim 13, wherein the liquid composition is maintained in a glass container.

27. The liquid composition of claim 15, wherein the liquid composition is maintained in a glass container.

28. The liquid composition of claim 16, wherein the liquid composition is maintained in a glass container.

29. The liquid composition of claim 17, wherein the liquid composition is maintained in a glass container.

30. The liquid composition of claim 12, wherein the liquid composition is maintained in a plastic container.

31. The liquid composition of claim 13, wherein the liquid composition is maintained in a plastic container.

32. The liquid composition of claim 15, wherein the liquid composition is maintained in a plastic container.

33. The liquid composition of claim 16, wherein the liquid composition is maintained in a plastic container.

34. The liquid composition of claim 17, wherein the liquid composition is maintained in a plastic container.

35. The method of claim 2, wherein the liquid composition is maintained at a temperature above 0° C. for at least 7 days without a decrease in viral activity of greater than about 20%.

36. The method of claim 2, wherein the liquid composition is maintained at a temperature of about 28° C. or higher for at least 7 days without a decrease in viral activity of greater than about 50%.

37. The method of claim 2, wherein the liquid composition is maintained at a temperature above 0° C. for at least 10 weeks without a decrease in viral activity of greater than about 50%.

38. The method of claim 2, wherein the liquid composition is a pharmaceutical composition, the liquid carrier is a pharmaceutically acceptable liquid carrier, and the adenovirus is an adenoviral gene transfer vector.

39. The method of claim 1, wherein the liquid is maintained in a glass container.

40. The liquid composition of claim 13, wherein the liquid composition can be maintained at a temperature above 0° C. for at least 7 days without a decrease in viral activity of greater than about 20%.

41. The liquid composition of claim 13, wherein the liquid composition can be maintained at a temperature of about 28° C. or higher for at least 7 days without a decrease in viral activity of greater than about 50%.

42. The liquid composition of claim 13, wherein the liquid composition can be maintained at a temperature above 0° C. for at least 10 weeks without a decrease in viral activity of greater than about 50%.

43. The liquid composition of claim 40, wherein the liquid composition has been maintained at a temperature above 0° C. for at least 7 days without a decrease in viral activity of greater than about 20%.

44. The liquid composition of claim 41, wherein the liquid composition has been maintained at a temperature of about 28° C. or higher for at least 7 days without a decrease in viral activity of greater than 50%.

45. The liquid composition of claim 42, wherein the liquid composition has been maintained at a temperature above 0° C. for at least 10 weeks without a decrease in viral activity of greater than about 50%.

46. The liquid composition of claim 13, wherein the liquid composition is a pharmaceutical composition, the liquid carrier is a pharmaceutically acceptable liquid carrier, and the adenovirus is an adenoviral gene transfer vector.

47. The liquid composition of claim 40, wherein the liquid composition is maintained in a glass container.

48. The liquid composition of claim 43, wherein the liquid composition is maintained in a glass container.

49. The liquid composition of claim 46, wherein the liquid composition is maintained in a glass container.

50. The liquid composition of claim 40, wherein the liquid composition is maintained in a plastic container.

51. The liquid composition of claim 43, wherein the liquid composition is maintained in a plastic container.

52. The liquid composition of claim 46, wherein the liquid composition is maintained in a plastic container.

53. The liquid composition of claim 14, wherein the trehalose is present in the liquid composition at a concentration of 4–6% (wt./vol.).

54. The liquid composition of claim 53, wherein the liquid composition further comprises polysorbate 80 at a concentration of about 0.001–0.01% (wt./vol.).

55. The method of claim 3, wherein the trehalose is present in the liquid composition at a concentration of 4–6% (wt./vol.).

56. The method of claim 55, wherein the liquid composition further comprises polysorbate 80 at a concentration of about 0.001–0.1% (wt./vol.).

57. The liquid composition of claim 54, wherein the liquid composition is maintained in a glass container.

58. The liquid composition of claim 54, wherein the liquid composition is maintained in a plastic container.

59. The method of claim 56, wherein the liquid composition is maintained in a glass container.

60. The method of claim 56, wherein the liquid composition is maintained in a plastic container.

61. The liquid composition of claim 54, wherein the liquid composition further comprises 75 mM NaCl.

62. The liquid composition of claim 54, wherein the liquid composition further comprises 10 mM Tris.

63. The method of claim 56, wherein the liquid composition further comprises 75 mM NaCl.

64. The method of claim 56, wherein the liquid composition further comprises 10 mM Tris.

* * * * *